United States Patent [19]
Rivera-Esquerdo

[11] Patent Number: 5,891,151
[45] Date of Patent: Apr. 6, 1999

[54] CASTING STAND FOR FOOT AND LEG

[76] Inventor: Wilfredo Rivera-Esquerdo, Condominio Montecillo No. 1, Apt. AB-2, Encantada, Trujillo Alto, Puerto Rico

[21] Appl. No.: 828,587

[22] Filed: Mar. 31, 1997

[51] Int. Cl.[6] .................................................. A61B 17/56
[52] U.S. Cl. .......................................... 606/105.5; 602/39
[58] Field of Search .................................. 606/53, 54, 60, 606/105, 105.5; 602/39

[56] References Cited

U.S. PATENT DOCUMENTS

| 743,663 | 11/1903 | Scheidl | 602/39 |
| 765,733 | 7/1904 | Hubbard | 602/39 |
| 2,035,952 | 3/1936 | Ettinger | 602/39 |
| 3,143,110 | 8/1964 | Stryker | 602/39 |

*Primary Examiner*—Guy V. Tucker
*Attorney, Agent, or Firm*—Thomas S. Hahn

[57] ABSTRACT

An apparatus for adjustably supporting and positioning a foot and leg to be cast that can be sterilized for use in a surgical environment. The apparatus including a foot support structure that in combination with a stand can be used to support and suspend the foot and also adjustably position the foot for applying cast material.

5 Claims, 3 Drawing Sheets

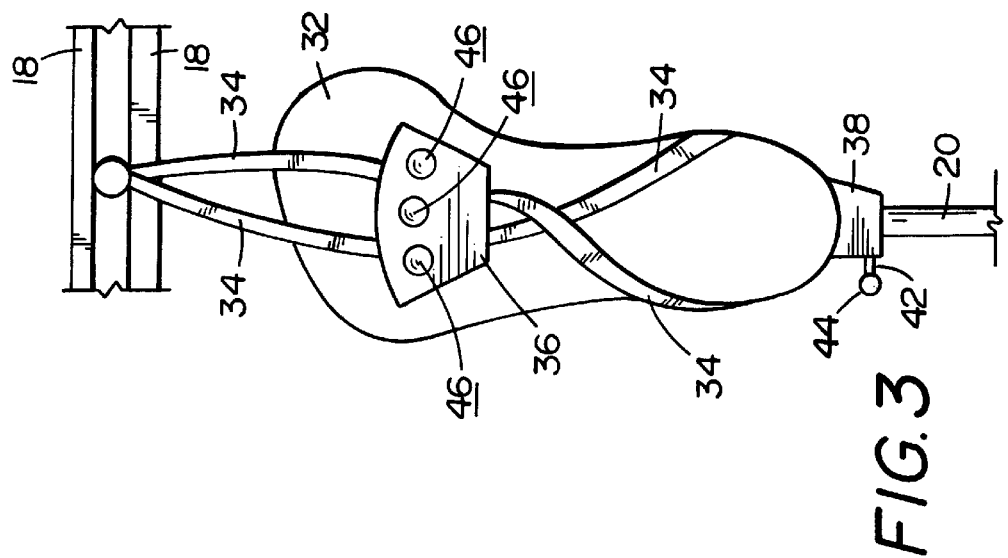
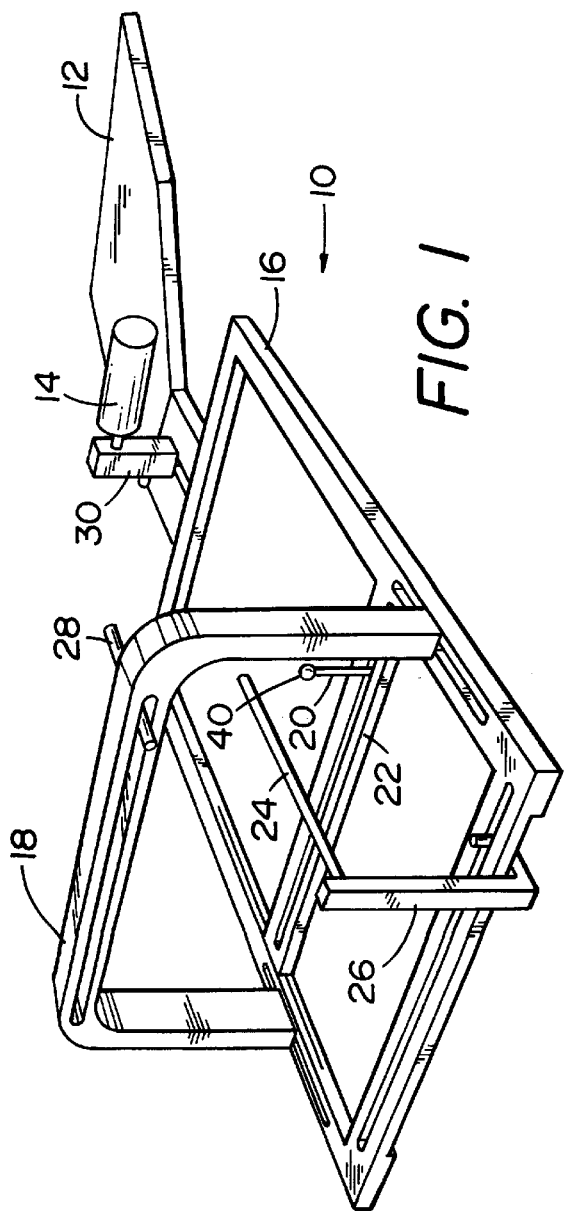
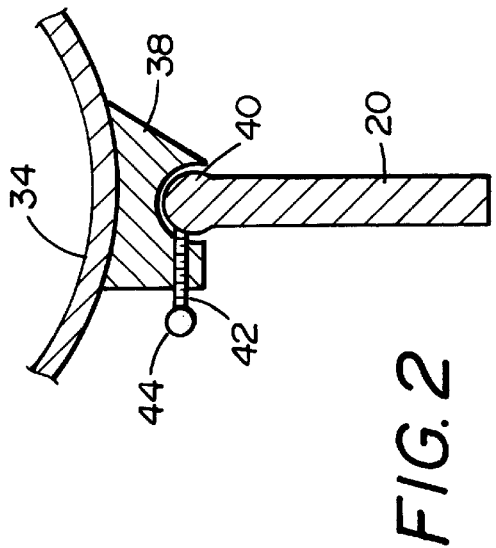

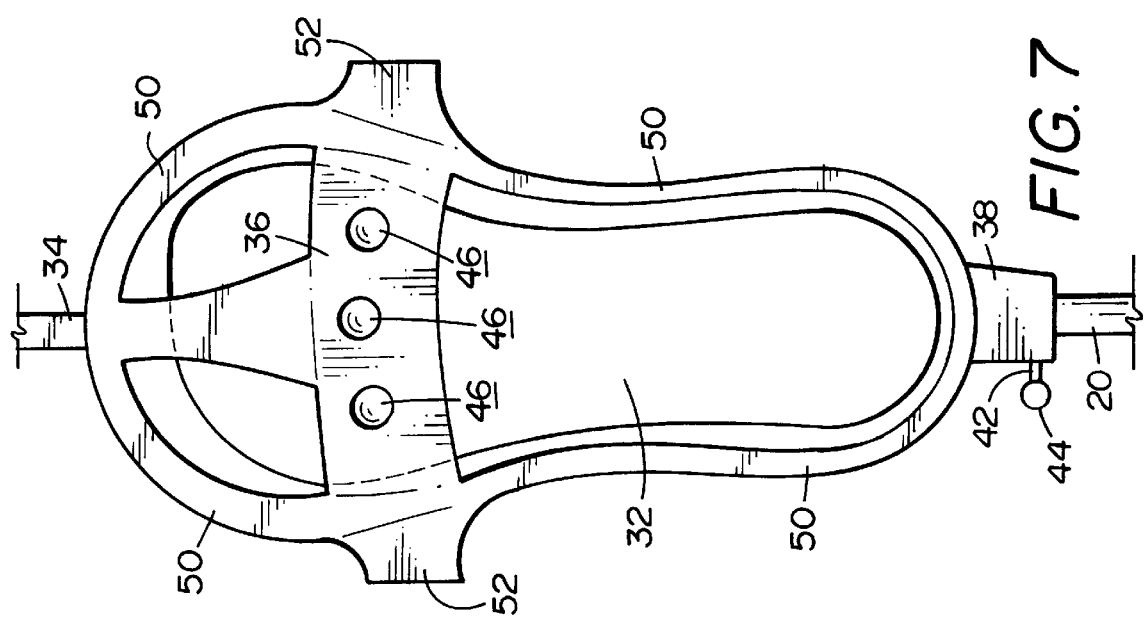
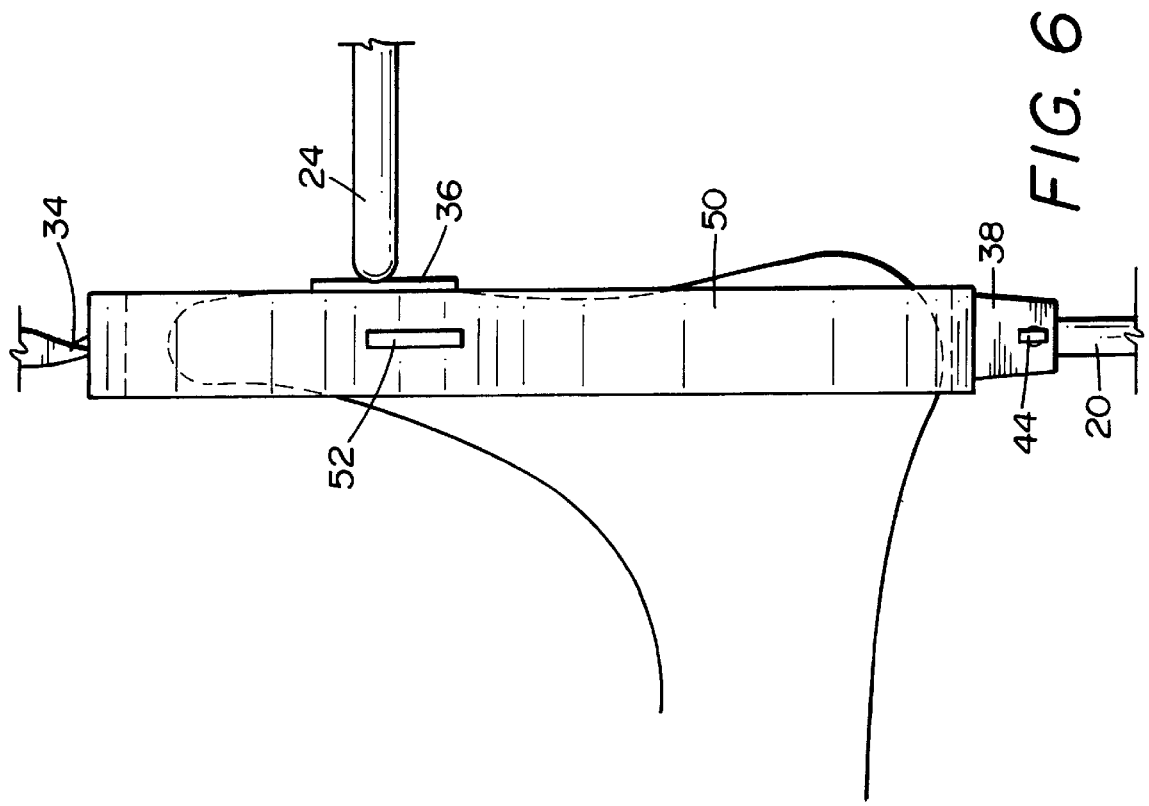

CASTING STAND FOR FOOT AND LEG

BACKGROUND OF THE INVENTION

This invention relates to an apparatus used to simultaneously position and support both the leg and foot of a patient during application of a cast, and more particularly the invention relates to an apparatus, usable in a sterile environment, that can be adjusted to position the supported leg and foot at any feasible orientation by movement of the leg and foot and maintain the selected leg/foot joint alignment during the time casting material is applied and allowed to set. The applied cast can be easily detached from the apparatus without structural degradation.

Human knee, ankle and foot joints permit a very wide range of devise positioning of the foot with respect to the leg. When set in casts to promote bone mending, however, it is necessary to select specific leg/foot joint orientations and then maintain the selected positioning while the cast material is both applied and allowed to set. The difficulties of adjusting leg/foot orientation and maintaining the selected positioning during casting are exasperated if the patient has additionally been or is treated surgically and is anesthetized. Accordingly, devices to adjustably position and support legs and feet during casting have been known for a long time. For example, U.S. Pat. No. 743,663, issued Nov. 10, 1903, describes a device for setting fractured legs during surgery. The described device is supposed to effect a linear stretching of the patient's leg to reposition fractured bones. Linear stretching is described as resulting from positioning a rod under the length of the leg and attaching an end of that first rod by a strap to the thigh of the patient. A second rod is then attached to a bandage buckled or laced to the foot. This second rod is further attached to the first rod with a threaded bolt structure so the second rod can pull the attached foot with respect to the leg as the threaded bolt structure is turned. Cast material is then supposed to be applied to the foot and leg while the foot is so pulled. After the cast is set, the first rod and other associated structures have to be removed through holes in the cast some of which must be bored and then later filled. Not addressed in any fashion because it cannot be in the U.S. Pat. No. 743,663 is how to orient a patient's leg/foot arrangement to different configurations other than a stretched one with the foot positioned in a stretched relationship to the leg and the sole of the foot oriented at an essentially ninety degree angle to the stretched longitudinal axis of the leg. Further restricting utility of the apparatus described in the U.S. Pat. No. 743,663 are the facts that after applied cast materials have set, it is necessary to remove rods, curved metal bars, and structural cross pieces from under the set cast through holes left in the cast or bored through the set cast. Unavoidably, such manipulations of a cast set on a patient's leg and foot risk further injury to the patient by removal of structures from under the cast, and also decrease the structural strength of the cast as a result, for example, of boring holes through the cast or applying the cast material so sizable that there are holes in the set cast. Attempting to later fill sizable holes in the cast or otherwise patch the cast can seal large openings needed to remove structural devices so as to prevent moisture and dirt from getting under the cast, but such repairs unavoidably cannot always restore the structural strength that a complete cast, without large bored or constructed openings, would have provided.

More recent attempts to design adjustable stands for positioning and supporting feet and legs to be cast have also failed to recognize and address the need to permit casting while supporting a foot and leg in such a manner that substantial openings in the cast are not required to remove sizable support stand structures. For example, U.S. Pat. No. 3,143,110, issued Mar. 1, 1962, describes a foot holder device for a cast table. The described foot holder device includes both a structure to support the heel area of a foot and a sole plate, identified for a preferred embodiment as being made of a flat metal plate, that is slidably attached to the heel support structure. According to the description provided in the U.S. Pat. No. 3,143,110, a cast is formed about a foot supported by such a foot holder device so that after the cast is set the sole plate is supposed to be slid out from the cast through a hole provided in the toe area and the heel support structure as an integral unit is supposed to be removed from an opening left in the cast as applied that extends about the entire heel area. In other words, the cast has to be formed so that the heel of the cast foot is not supported in the cast. As with the earlier patented device, the U.S. Pat. No. 3,143,110 admits in its disclosures that after the cast is set and the holder device is removed, additional cast material can be coated over the pare portions of the heel and toes of the foot. Such patching cannot restore the structural strength that a complete cast, without constructed openings, would have provided. Additionally, as with the earlier patent, the U.S. Pat. No. 3,143,110 describes the foot holder device as only providing a single fixed angle for the sole of the supported foot to the longitudinal axis of the leg.

SUMMARY OF THE INVENTION

In contrast to the prior art devices, the present invention provides for full adjustment of foot and leg positioning, even during or immediately after surgery, so that cast material can be rolled onto the supported foot and leg. Additionally, the present invention only requires two cylindrical openings to be provided in the cast. (Cylindrical openings, whether circular or other shaped, produce the minimal degradation of the physical support strength of a structure as compared to any other shaped opening, e.g., cubical, triangular or rectangular). Both of these openings can be 2.0 centimeters (cm) or less in diameter. One opening is for a heel support rod, and the other opening is for a frontal and sagittal plane stabilizer rod that is positioned at the metatarsal area of the foot. The first of the openings is substantially at the center of the back of the heel area of the foot, and the other is in the metatarsal area of the sole of the foot. These openings are so positioned as not to degrade the longitudinal support strength of the applied cast. Both rods can both be removed from the cast before it has set and the small openings can then be covered with fresh material. The combination of the small size, cylindrical shape and locations for the holes assures that the structural strength of the final cast is not compromised with respect to a comparable cast without openings.

The present invention includes a stand upon which a patient can be laid so that the leg and foot to be cast are supported. The thigh of the leg to be cast is put on a cushion roll, and the foot can be supported by several alternative structures, including a foot strap, heel cup or foot support with toe protector (all described below). Each of these structures include a socket attachment at the base area which is positioned adjacent the heel. The socket attachment is sized so that a ball shaped at the end of a heel support rod can be snap-fitted into the socket. By mounting the heel support rod from the stand of the present invention and snap-fitting the socket attachment with its foot support structure onto the heel support rod, the foot to be cast can be supported. Additionally, the foot support structures also include metatarsal plates that are positioned at the metatarsus area of the foot to be cast. The metatarsal plates include cup-like indentations or detents on the surface opposite the sole of the foot to be cast. A stabilizer rod also adjustably mounted from the stand of the present invention is positioned so one end is positioned in one of the detents in the metatarsal plate. Finally, a strap extension from each of the foot support structures can be attached to a support rod also adjustably mounted from the stand of the present invention. Thus, the foot is (i) supported by the heel support rod, (ii) stabilized in an articulated position by a stabilizer rod positioned against the metatarsal plate, and can be (iii) suspended via the strap and support rod to which it is attached.

Cast material can now be applied to the so positioned and stably supported foot and leg to be cast. The heel support rod and stabilizer rod, which are made of structurally strong material such as stainless steel, are then removed from the cast by pulling the stabilizer rod away from the metatarsal plate and pulling the heel support rod so that it snaps out of the socket attachment. The strap is detached from its support rod, and the extra length strap extending out of the cast is cut off at the surface of the cast.

This invention provides not only an apparatus that can be sterilized for use in a surgically clean environment, but one that provides for complete adjustability to effectively and stably position the foot and leg to be cast and a system which, after the cast material is applied, can be detached by extracting two rods of 2 cm diameter or less through holes that are perpendicular to the surface of the cast. Such perpendicular extraction of the rods effectively eliminates the possibility of injury to the patient that might be related to the extractions.

BRIEF DESCRIPTION OF THE DRAWINGS

Corresponding components in the various figures are either designated by the same reference numerals or, if different reference numerals are used, their relationship is identified in the text. The various objectives, advantages and novel features of the invention will become more readily apprehended from the following detailed description when taken in conjunction with the appended drawings, in which:

FIG. 1 is a perspective diagram showing an overview of the casting stand according to the invention;

FIG. 2 is a cross-sectional view of the a heel support socket with attached foot strap on the back of a patient's heel;

FIG. 3 is a partial plan view showing the sole of a foot supported and suspended using a foot strap with attachments of the invention;

FIG. 6 is a partial plan view showing the side of a foot supported and suspended using a foot support with toe protector and attachments according to the invention, and FIG. 7 is a partial plan view showing the sole of a foot supported and suspended using a foot support with toe protector and attachments according to the invention.

DETAILED DESCRIPTION OF THE INVENTION

Figure 5:
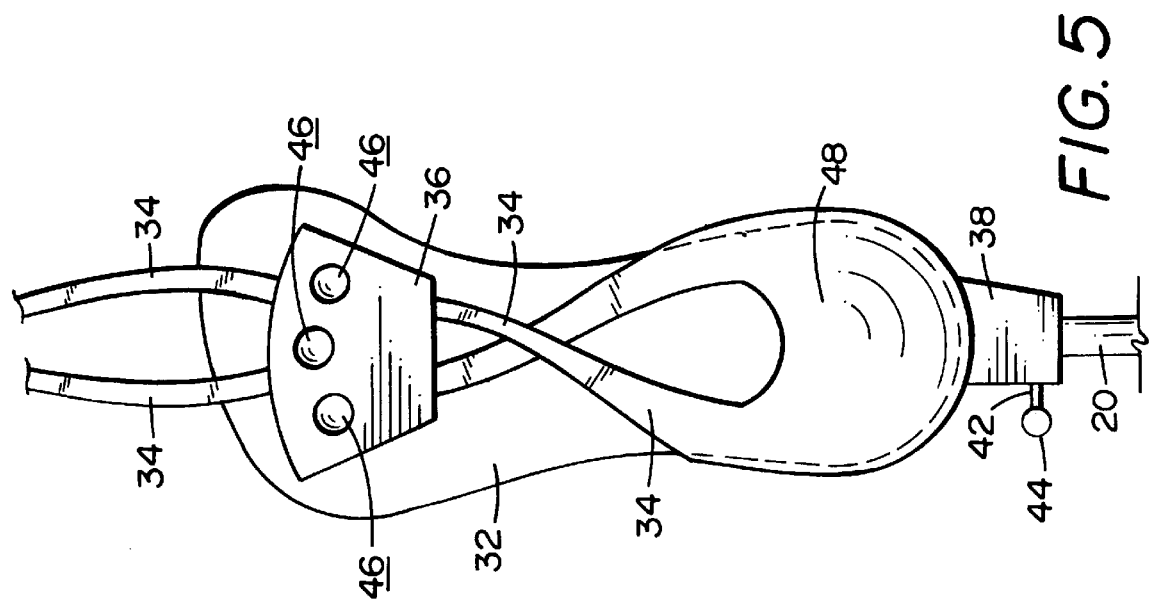
FIG. 5 is a partial plan view showing the sole of a foot supported and suspended using a cup with foot strap and attachments according to the invention.
Figure 4:
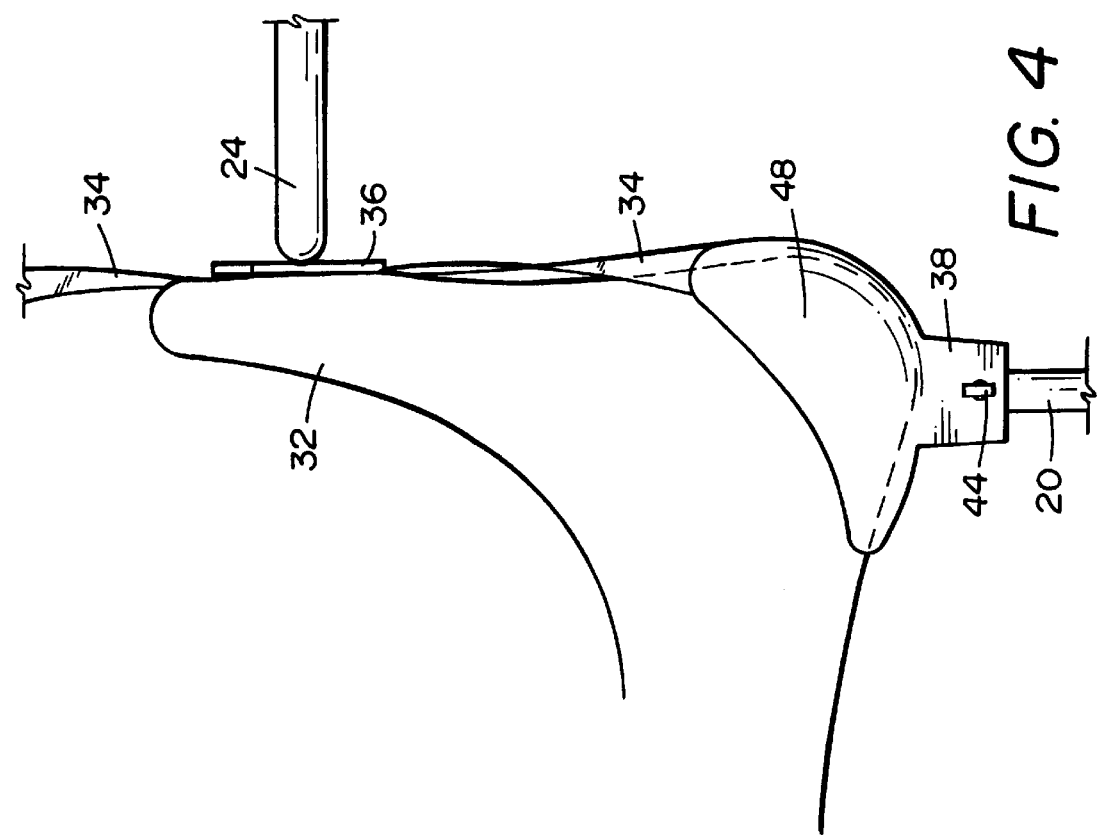
FIG. 4 is a partial plan view showing the side of a foot supported and suspended using a cup with foot strap and attachments according to the invention.

Referring now to the drawings, a perspective view of a casting stand for a foot and leg according to the invention are shown in FIG. 1 and generally designated by reference numeral 10. This stand 10 is used to support both the leg and foot of a patient during application of casting material and setting of the cast. Further, this stand 10, as described below, is capable of adjustments to orient the supported foot relative to the supported leg in all positions permitted by the ankle and other joints.

The stand 10 is portable and can be placed on any flat surface capable of supporting a patient such as beds, examining tables, surgical tables and even stretchers. Included as part of the stand 10 are: (i) an anchor surface 12; (ii) a cushion roll 14; (iii) a tower base 16; (iv) a tower 18; (v) a heel support rod 20; (vi) a heel support base 22; (vii) a frontal and sagittal plane stabilizer rod 24; (viii) stabilizer rod support 26; and (ix) a foot strap support rod 28.

The anchor surface 12 is made of any material capable of supporting a patient's buttocks and leg. Suitable materials must be both capable of stably supporting the patient's weight and also capable of effective and efficient cleaning. Both metals, such as stainless steel or aluminum, and plastics are classes of suitable materials for making anchor surface 12.

Adjustably mounted above the anchor surface 12 is a horizontally positioned cushion roll 14 used to comfortably and fully support the posterior portion of the thigh of the leg to which the cast is to be applied. As with the anchor surface 12, the cushion roll 14 is made of structurally sturdy materials capable of supporting a patient's weight and also capable of being effectively and efficiently cleaned. The cushion roll 14 is preferably covered with a compressible smooth surface plastic material. The cushion roll 14 is mounted above the anchor surface 12 from a cushion roll support 30. As shown in FIG. 1, the roll cushion 14 is mounted to support a left leg, but this mounting of the cushion roll 14 can be reversed (mounting structure specifics not shown) so as to be capable of supporting a right leg. Additionally, the height of cushion roll 14 above the anchor surface 12 can be adjusted to provide necessary positioning of the leg to effect the correct orientation.

The tower base 16 with all the attached structures, including the tower 18, heel support rod 20, heel support base 22, frontal and sagittal plane stabilizer rod 24, and foot strap support rod 28, of the stand 10 are detachable from the anchor surface 12. Having the anchor surface 12 be detachable permits sterilization, e.g., in an autoclave, of the tower base 16, tower 18, heel support rod 20, frontal and sagittal plane stabilizer rod 24, stabilizer rod support 26, and foot strap support rod 28.

The structures for attachment and detachment of the tower base 16 to and from the anchor surface 12 can be of any adequate known type such as screws, bolts and nuts or pins. Because the tower base 16 and associated structures can be sterilized, the stand 10 can be used during or after surgery when it is necessary to apply cast material.

All of the heel support 20 rod, heel support base 22, frontal and sagittal plane stabilizer rod 24, and foot strap support rod 28 are mounted so their positions can be adjusted and then fixed by, for example, known arrangements such as tightening threaded screws with nuts in slotted grooves (not shown). Providing the capability for these variable adjustments not only permits the stand structure to be adjusted to position and support feet and legs of differing size but also to support and position either a right or a left foot in conjunction with the appropriately positioned cushion roll 14 to support the necessary leg.

In use a patient is positioned on the stand 10 with the posterior portion of the thigh supported by the cushion roll 14 and the heel of the foot 32 resting on the heel support rod 20 (with additional structure that is described below) as, for example, partially shown in FIG. 2. A known stockinette or similar sock-like cover used to decrease itching from cast padding can be put on the foot 32 before the foot 32 is mounted on the heel support rod 20. Besides supporting the weight of the foot 32 on heel support rod 20, a system for suspension support can also be provided from the foot strap support rod 28. Various structures can be used to provide this suspension support. For example, a preferred structural embodiment to provide such suspension support is a foot strap 34 with metatarsal plate 36 and heel support rod socket 38 as shown in FIGS. 2 and 3. The foot strap 34 can be made of any non-stretchable material capable of being sterilized which is strong enough to support the weight of a foot 32. Attached to the foot strap 34 is a metatarsal plate 36, which, when mounted on the foot 32 to be cast, is positioned against the metatarsus area. The metatarsal plate 36 is slidably mounted on the foot strap 34 by including slots (not shown) in the metatarsal plate 36 through which foot strap 34 can slide with a friction fit. This adjustable mounting of the metatarsal plate 34 to the foot strap 34 permits the fitting of a foot strap 34 with metatarsal plate 36 to different foot sizes. Again, the metatarsal plate 36 is made of a sterilizable material such as plastic. Also mounted to foot strap 34 is a heel support rod socket 38. As shown in cross-section in FIG. 2, the heel support rod socket 38 is sized to accept in a snap-fit fashion the end of heel support rod 20 which is made in a ball shape to snap and securely fit in the heel support rod socket 38. The heel support rod socket 38 can be made of known plastics to permit the snap-fit and durability for sterilization. This arrangement to fully support the weight of the foot 32 also permits the foot to be rotated about three mutually perpendicular axes associated with the ankle joint. Any selected orientation for foot 32 can then be maintained by tightening set screw 42 against the ball 40 using the wing 44. To assure the necessary structural strength to support foot 32, the heel support rod 20 is made of a durable and sterilizable material, such as stainless steel, with the ball 40 end integrally fabricated. By using such materials, the heel support rod 20 can have a diameter of 2 cm or less and still adequately support a foot 32. The 2 cm diameter is not critical other than to be as small as is required to provide structural strength and require the least size opening in the cast to be applied to the foot 32.

After the foot strap 34 is mounted on the foot 32 by having the section with the heel support rod socket 38 of the foot strap 34 positioned under the heel and the foot 32 is positioned on the heel support rod 20, the length of foot strap 34 above the toes is fixed by, for example, tying to the foot strap support rod 28 so that the supported foot 32 is suspended over the heel support rod 20. The fixing of the foot strap 34 to the foot strap support rod 28 can be by use of, for example, a friction clamp (not shown), as are known, mounted on the foot strap support rod 28, or other known mechanisms. Such a friction clamp would include a pivotally mounted lever that, when closed down against the foot strap 34, would firmly attach the foot strap 34 to the foot strap support rod 28.

At this stage of the positioning process or before the foot strap 34 is attached to the foot strap support rod 28, the frontal and sagittal plane stabilizer rod 24 is adjustably positioned against the metatarsal plate 36 in one of the provided detents 46 which are indentations in the metatarsal plate 36 surface. The detent 46 to be used is selected on the basis of the desired positioning of the foot. Both the height of the frontal and sagittal plane stabilizer rod 24 above the tower base 16 and the length of the frontal and sagittal plane stabilizer rod 24 from the stabilizer rod support 26 are adjustable. Specifically, the position of the frontal and sagittal plane stabilizer rod 24 is adjusted to mount in the selected detent 46 so that both the proper dorsiflexion (sagittal plane correction; foot going backwards) and eversion (pronation) or inversion (supination), i.e., frontal plane correction, are achieved. As with the heel support rod 20, frontal and sagittal plane stabilizer rod 24 is made of a durably and sterilizable material, such as stainless steel, and should be of a 2 cm or less diameter.

A patient's leg and foot 32 can be positioned in any desired orientation, with the supports for the leg and foot 32 provided by the stand 10 and with metatarsal plate 36 even while the patient is anesthetized and the cast material is being applied and allowed to set.

At this point cast padding (known) is rolled on the areas of the foot 32 and leg to be cast, which has already been covered with stockinette, and then any of the known cast materials can be rolled on the positioned and supported leg and foot 32. Alternatively, the foot 32 and leg can be positioned, including mounting a foot strap 34 and metatarsal plate 36, without stockinette covering the skin and then after the foot 32 and leg are positioned in the stand 10, stockinette can be applied to cover both skin and the support structures, such as foot strap 34 and metatarsal plate 36. A surgeon can use this alternative process to position the leg and foot 32 during and/or after surgery when maximum sterilization is needed. The cast material is rolled about the ankle and foot 32 to encase the padding, stockinette, the foot strap 34, heel support rod socket 38, and metatarsal plate 36 against the foot 32. This application of cast material is made so that after the cast has set, the portion of the foot strap 34 mounted from the foot strap support rod 28 can be cut off at the surface of the set cast. The set screw 32 if previously tightened is loosened before cast material is applied, and after cast material is applied, both the heel support rod 20 and frontal and sagittal plane stabilizer rod 24 are removed. After such removal, the small openings in the cast can be covered. Thus, a cast can be set about the foot 32 which fully supports and protects the foot 32 and leg. Additionally, because of the wide latitude of adjustments permitted by the stand 10, the casting material can be applied above or below the knee and while the knee is bent (gastrocnemius muscle laxed) or the knee is straight (gastrocnemius muscle stretched).

An alternative support/suspension system can be used to provide even further support for the foot 32 while the cast naterial is being applied. This alternative system uses a cup 48 positioned adjacent the heel with a foot strap 34 molded in as part of the cup 48 and extending from the cup 34 with metatarsal plate 36 slidably attached to the foot strap 34. Attached to the cup 48 so it will be positioned at the back of the heel of the foot 32 to be supported is a heel support rod socket 38. The cup 48 should be made of a pliable material that will be comfortable against the skin of the foot 32 when encased in a cast. Alternatively, as discussed above, the heel area can be covered with a stockinette before the cup 48 is mounted on the heel. This material must additionally be sterilizable if it is to be used in a surgical environment. In those situations when the cup 48 is positioned against the skin, the cup 48 material must also be hypoallergenic. An acceptable material in those situations would be silicone. The cup 48, foot strap 34, heel support rod socket 38 and metatarsal plate 36 are used to support, position and suspend the foot to be cast in the same manner as the foot strap 34, heel support rod socket 38 and metatarsal plate 36 combination. Similarly, the cup 48, foot strap 34, heel support rod socket 38 and metatarsal plate 36 are encased within the cast, and after the cast is set, the excess foot strap 34 material extending from the cast is cut off.

Still another alternative support/suspension system that can be used to support the foot 32 is shown in FIGS. 6 and 7. Here, a foot support with toe protector 50 is provided. This system uses a laterally encasing structure about the foot 32. The foot support with toe protector 50 includes a metatarsal plate 36 and a heel support rod socket 38. The entire foot support with toe protector 50 can be made of a durable and sterilizable plastic. Additionally, the foot support with toe protector 50 can be made of an hypoallergenic material so that stockinette can be applied about the foot 32 when the foot support with toe protector 50 is already positioned against the skin. A length of foot strap 34 can be extended from the top of the foot support with toe protector 50 to support the structure from the foot strap support rod 28. The foot support with toe protector 50 is used to support, position and suspend the foot 32 to be cast in the same manner as the foot strap 34, heel support rod socket 38 and metatarsal plate 36 combination. Cast material is rolled over the foot support with toe protector 50 after the foot 32 and leg are properly positioned, and at least one wing extension 52 is provided from the foot support with toe protector 50 so that the positioning of the foot support with toe protector 50 is fixedly stabilized in the cast, and the foot 32 and leg encased in the cast are adequately and comfortably restrained to permit effective bone mending without the foot support with toe protector 50 being loose inside the cast. Any excess length of wing extensions 52 protracting from the outer surface of the cast after it is set can be cut off, as will be the foot strap 34.

The above discussion and related illustrations of the present invention are directed primarily to preferred embodiments and practices of the invention. However, it is believed that numerous changes and modifications in the actual implementation of the concepts described herein will be apparent to those skilled in the art, and it is contemplated that such changes and modifications may be made without departing from the scope of the invention as defined by the following claims.

What is claimed is:

1. A foot positioning stand for maintaining a foot in an optimal joint alignment position during the application of a cast, said foot positioning stand comprising:

a foot support means for supporting and positioning the foot to be cast, said foot support means including (a) heel support rod attachment means, and (b) a metatarsal positioning plate means;

a heel support rod means that can be adjustable moved to different positions and fixedly mounted at the selected position, said heel support rod means being detachably attached to said heel support rod attachment means to support the weight of the foot to be cast, and a frontal and sagittal plane stabilizer rod means that can be adjustably moved to different positions and fixedly mounted at the selected position, said stabilizer rod means having an end that can be detachably positioned against said metatarsal positioning plate means to fix the position of the frontal and sagittal plane of the positioned foot.

2. A foot positioning stand according to claim 1 further including a strap attachment means extending from said foot support means that can be detachably attached to a strap support rod that can be moved to different positions.

3. A foot positioning stand according to claim 1 wherein said foot support means includes a (a) foot strap means, (b) metatarsal positioning plate means, and (c) heel support rod attachment means.

4. A foot positioning stand according to claim 1 wherein said foot support means includes a (a) heel cup means, (b) foot strap means, and (c) heel support rod attachment means.

5. A foot positioning stand according to claim 1 wherein said foot support means includes a (a) foot support with toe protector means, (b) foot strap means, and (c) heel support rod attachment means.

* * * * *